(12) United States Patent
Stan et al.

(10) Patent No.: US 7,735,203 B2
(45) Date of Patent: Jun. 15, 2010

(54) PROCESS FOR PRODUCING FOLDED AND COMPRESSED TAMPONS

(75) Inventors: Mihai Alin Stan, Brussels (BE); Steven Ray Gilbert, Fairfield, OH (US); Holger Wendt, Budapest (HU)

(73) Assignee: The Procter & Gamble Company, Cincinnati, OH (US)

( * ) Notice: Subject to any disclaimer, the term of this patent is extended or adjusted under 35 U.S.C. 154(b) by 973 days.

(21) Appl. No.: 11/504,983

(22) Filed: Aug. 16, 2006

(65) Prior Publication Data

US 2008/0065041 A1    Mar. 13, 2008

(51) Int. Cl.
*A61F 13/20*   (2006.01)
(52) U.S. Cl. ....................................................... 28/118
(58) Field of Classification Search ................... 28/118, 28/119, 120, 121, 122, 123, 116; 604/385.17, 604/385.18, 904; 264/320, 323, 324, 325, 264/327
See application file for complete search history.

(56) References Cited

U.S. PATENT DOCUMENTS

| | | | | |
|---|---|---|---|---|
| 2,336,744 A | * | 12/1943 | Manning | 28/119 |
| 2,425,004 A | * | 8/1947 | Rabell | 28/118 |
| 3,422,496 A | * | 1/1969 | Messing et al. | 28/118 |
| 3,431,909 A | | 3/1969 | Krusko | |
| 3,610,243 A | | 10/1971 | Jones, Sr. | |
| 3,643,661 A | | 2/1972 | Crockford | |
| 3,875,615 A | * | 4/1975 | Muckenfuhs | 28/119 |
| 3,971,378 A | | 7/1976 | Krantz | |
| 4,067,087 A | * | 1/1978 | Mast, Jr. | 28/118 |
| 4,109,354 A | * | 8/1978 | Ronc | 28/119 |
| 4,518,451 A | | 5/1985 | Luceri et al. | |
| 4,627,849 A | | 12/1986 | Walton | |
| 4,951,368 A | | 8/1990 | Heinen | |
| 5,084,038 A | | 1/1992 | Sheldon et al. | |
| 5,165,152 A | * | 11/1992 | Kramer et al. | 28/118 |
| 6,433,246 B1 | | 8/2002 | Nguyen et al. | |
| 6,488,670 B1 | | 12/2002 | Schild et al. | |
| 6,554,814 B1 | | 4/2003 | Agyapong | |
| 6,682,513 B2 | | 1/2004 | Agyapong | |
| 6,719,743 B1 | | 4/2004 | Wada | |
| 6,740,070 B2 | | 5/2004 | Agyapong | |

(Continued)

FOREIGN PATENT DOCUMENTS

EP   0 685 213 A   12/1995

OTHER PUBLICATIONS

Patent Cooperation Treaty, Applicant's File Reference: 10526Q, PCTIB2007/053258 (6 pages).

(Continued)

*Primary Examiner*—Amy B Vanatta
(74) *Attorney, Agent, or Firm*—James E. Oehlenschlager; Roddy M. Bullock (57) ABSTRACT

A method and apparatus for producing a stabilized tampon from a tampon pledget. The method includes the steps of providing a tampon pledget; providing a compression mold having disposed therein a plurality of fluid communication passages; moving the tampon pledget into the compression mold, the compression mold being in an open position; applying a force delivery means through the fluid communication passages to deform the tampon pledget into a pre-folded shape; and compressing the pledget in the compression mold by closing the compression mold into a closed position to form a folded, compressed tampon.

13 Claims, 5 Drawing Sheets

U.S. PATENT DOCUMENTS

| | | | |
|---|---|---|---|
| 6,748,634 B2 | 6/2004 | Nguyen et al. | |
| 6,824,536 B2 | 11/2004 | Randall et al. | |
| 6,889,409 B2 * | 5/2005 | Friese et al. | 28/118 |
| 7,047,608 B2 | 5/2006 | Sageser et al. | |
| 7,120,977 B2 * | 10/2006 | Bittner et al. | 28/118 |
| 7,124,483 B2 * | 10/2006 | Prosise et al. | 28/118 |
| 7,472,463 B2 * | 1/2009 | Gilbert et al. | 28/118 |
| 2001/0009711 A1 | 7/2001 | Latimer et al. | |
| 2003/0172504 A1 | 9/2003 | Sageser et al. | |
| 2004/0226152 A1 | 11/2004 | Prosise et al. | |
| 2004/0244165 A1 | 12/2004 | Bittner et al. | |
| 2005/0027275 A1 | 2/2005 | Wasson et al. | |
| 2005/0096619 A1 | 5/2005 | Costa | |
| 2005/0256686 A1 | 11/2005 | Stabelfeldt et al. | |
| 2005/0264561 A1 | 12/2005 | Anast et al. | |
| 2005/0264562 A1 | 12/2005 | Macura et al. | |
| 2005/0264563 A1 | 12/2005 | Macura et al. | |
| 2005/0264572 A1 | 12/2005 | Anast et al. | |
| 2005/0267613 A1 | 12/2005 | Anast et al. | |
| 2005/0267614 A1 | 12/2005 | Looney et al. | |
| 2005/0267615 A1 | 12/2005 | Lavash et al. | |

OTHER PUBLICATIONS

PCT International Search Report dated Dec. 3, 2008.
"Diapers: Better by Design with CFD", 2000 Fluent Inc., Spring, 2000.
"New Developments in the Assessment of Protective Fabrics Using Computational Models", Hill, Ph.D. et al., INJ Winter 2004, pp. 22-30.
"Computational Fluid Dynamics Modeling of Fabric Systems for Intelligent Garment Design", Barry et al., MRS Bulletin/Aug. 2003, pp. 568-573.

* cited by examiner

PROCESS FOR PRODUCING FOLDED AND COMPRESSED TAMPONS

FIELD OF THE INVENTION

The invention relates to a process for folding and compressing tampon pledgets to make compressed tampons.

BACKGROUND OF THE INVENTION

Tampons are well known as absorbent articles, and specifically as feminine hygiene articles effective in the absorption of menses inside the vagina. Tampons are generally cylindrically-shaped, compressed batts of absorbent fibers that expand upon being wetted in use. For example, once inserted inside the vagina, tampons tend to expand as fluid is absorbed, thereby increasing in volume to fill more of the space within the vagina. As the tampon expands, more surface area is exposed that can contact the walls of the vagina, thereby intercepting more fluid and preventing fluid escape and leakage.

In many instances tampon tends to be constrained by the walls of the vagina such that maximum expansion, and therefore, maximum fluid interception, is hindered. A vagina can have a shape of a flattened pouch, for example, such that a rolled, compressed tampon that tends to expand by radial expansion can be hindered from full expansion against the closely-spaced side walls of the vagina.

Tampons can be designed to expand width-wise, that is, by expanding in one lateral dimension greater than in another. In one embodiment, a tampon can be formed from a generally flattened batt or pledget of fibers. The flattened pledget can be fan-folded in a generally zigzag cross sectional configuration and compressed into a tampon, such that the tampon expands by unfolding primarily in one direction.

One problem with fan-folded tampon pledgets is the cost and complexity involved in making such tampons. Rather than simply compress a batt of fibers by folding and compressing in a generally random manner, fan-folding requires that prior to compression in a compression mold the batt be first folded, or partially folded, such that upon compression the folds are captured in the compressed structure. Such pre-folding is difficult to achieve with current tampon manufacturing equipment. Further, such tampon folding is difficult to achieve in a controlled manner such that the folding, and therefore, the expansion response is uniform and/or predictable.

Accordingly, there is a continuing need for a method and device for pre-folding and managing a controlled fold in a tampon pledget prior to compression.

Further, there is a continuing need for a method and device for controlled folding of a tampon pledget in such a manner that the expansion response of the tampon in use is relatively uniform with respect to known methods of making tampons from generally flat tampon pledgets.

Further, there is a continuing need for a method and device for controlled folding of a tampon pledget in such a manner that the expansion response of the tampon in use is relatively predictable with respect to known methods of making tampons from generally flat tampon pledgets.

SUMMARY OF THE INVENTION

A method and apparatus for producing a stabilized tampon from a tampon pledget is disclosed. The method includes the steps of providing a tampon pledget; providing a compression mold having disposed therein a plurality of fluid communication passages; moving the tampon pledget into the compression mold, the compression mold being in an open position; applying a force delivery means through the fluid communication passages to deform the tampon pledget into a pre-folded shape; and compressing the pledget in the compression mold by closing the compression mold into a closed position to form a folded, compressed tampon.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying Figures, in which:

DETAILED DESCRIPTION OF THE INVENTION

As used herein, "compression" refers to the process of pressing, squeezing, compacting or otherwise manipulating the size, shape, and/or volume of a material to obtain a tampon having a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

The term "joined" or "attached," as used herein, encompasses configurations in which a first element is directly secured to a second element by affixing the first element directly to the second element; configurations in which the first element is indirectly secured to the second element by affixing the first element to intermediate member(s) which in turn are affixed to the second element; and configurations in which the first element is integral with the second element; i.e., the first element is essentially part of the second element.

As used herein, "mold" refers to a structure for shaping a tampon pledget during compression and/or retaining the shape for a compressed tampon pledget subsequent to compression during the stabilization process. Molds have an inner surface defining an inner cavity and an outer surface. The inner cavity is structured to define or mirror the desired shape of the compressed absorbent tampon pledget.

The inner cavity of a mold may be profiled to achieve any shape known in the art including, but not limited to, cylindrical, rectangular, triangular, trapezoidal, semi-circular, hourglass, serpentine or other suitable shapes. The inner cavity of a mold can have longitudinally-extending ridges and grooves to form a shaped tampon exhibiting longitudinally-oriented "flutes" that can be generally straight or can be in a generally spiral orientation. The outer surface of the mold is the surface external to the inner surface and can be profiled or shaped in any manner, such as, rectangular, cylindrical or oblong. The mold may comprise one or more members.

One mold used in the present invention may be a unitary mold, comprising one member, or "split cavity mold" as those disclosed in U.S. patent application Ser. No. 10/150,050 entitled "Substantially Serpentine Shaped Tampon," and U.S. patent application Ser. No. 10/150,055, entitled "Shaped Tampon," both filed on Mar. 18, 2002. Whereas unitary molds may be used for less complex shapes such as cylindrical or substantial cylindrical.

The term "permeable," as used herein, refers to the ability of a material to allow the spread or infusion of a gas through the material's composition. A material may be permeable due to its composition or the material may be fabricated from impermeable material then modified to become permeable, either chemically, mechanically, or electrically, such as, for example by acid etching, drilling, or aperturing.

As used herein the terms "pledget" or "tampon pledget" are intended to be interchangeable and refer to a construction of absorbent material prior to the compression of such construction into a tampon. The apparatus and method of the present invention are particularly useful for making compressed tampons from generally flattened tampon pledgets.

The term "pores," as used herein, refers to small openings or interstices that connect the inner surface of the mold with the outer surface of the mold in fluid communication, i.e., admitting the passage and infusion of gases into and through a compressed tampon pledget contained within the inner cavity of the mold.

As used herein, "self-sustaining" is a measure of the degree or sufficiency to which the tampon retains its compressed form after stabilization such that in the subsequent to the absence of external forces, the resulting tampon will tend to retain its vaginally insertable shape and size. For tampons, it is found that control of the level of moisture within the tampon is a factor for helping the tampon to retain its shape subsequent the absence of the external compression forces. It will be understood by one of skill in the art that this self-sustaining form need not, and preferably does not, persist during actual use of the tampon. That is, once the tampon is inserted into the vagina or other body cavity and begins to acquire fluid, the tampon will begin to expand and may lose its self-sustaining form.

The term "shaped tampons," as used herein, refers to compressed tampon pledgets having either a substantially serpentine shape, a "undercut" or "waist". The phrase "substantially serpentine" refers to a non-linear dimension between any two points spaced at least about 5 mm apart. The term "undercut" refers to tampons having a protuberance or indentation that impedes the withdrawal from a unitary mold. For example, shaped tampons may be hourglass shaped having at least one perimeter in the center of the tampon or "waist" that is less than both an insertion end perimeter and a withdrawal end perimeter.

As used herein, the term "split cavity mold" is a mold comprised of two or more members that when brought together complete the inner cavity of the mold. Each member of the split cavity mold comprises at least a portion of the inner surface that when brought together or closed completes the mold structure. The split cavity mold is designed such that at least two or more of the mold members can be at least partially separated, if not fully separated, typically after the tampon has acquired a self-sustaining shape, to expand the cavity volume circumscribed by the inner surface(s) thus permitting the easier removal of the tampon from the mold. Partial separation can occur when only a portion of two mold members are separated while other portions of the two mold members remain in contact. Where each member's inner surface portion joins the inner surface portion of another member, those points of adjacency can define a straight line, a curve, or another seam of any convoluted intersection or seam of any regular or irregular form. The elements of the split cavity in some embodiments may be held in appropriate position relative to each other by linking elements of any form including bars, rods, linked cams, chains, cables, wires, wedges, screws, etc.

The term "stabilized," as used herein, refers to a tampon in a self-sustaining state wherein it has overcome the natural tendency to re-expand to the original size, shape and volume of the absorbent material and overwrap, which comprise the tampon pledget.

As used herein the term "tampon," refers to any type of absorbent structure that is inserted into the vaginal canal or other body cavities for the absorption of fluid therefrom, to aid in wound healing, or for the delivery of active materials, such as medicaments, or moisture. The tampon may be compressed into a generally cylindrical configuration in the radial direction, axially along the longitudinal axis or in both the radial and axial directions. While the tampon may be compressed into a substantially cylindrical configuration, other shapes are possible. These may include shapes having a cross section that may be described as rectangular, triangular, trapezoidal, semi-circular, hourglass, serpentine, or other suitable shapes. Tampons have an insertion end, withdrawal end, a length, a width, a longitudinal axis and a radial axis. The tampon's length can be measured from the insertion end to the withdrawal end along the longitudinal axis. A typical compressed tampon for human use is 30-60 mm in length. A tampon may be straight or non-linear in shape, such as curved along the longitudinal axis. A typical compressed tampon is 8-20 mm wide. The width of a tampon, unless otherwise stated in the specification, corresponds to the length across the largest cylindrical cross-section, along the length of the tampon.

The term "vaginal cavity," "within the vagina," and "vaginal interior," as used herein, are intended to be synonymous and refer to the internal genitalia of the mammalian female in the pudendal region of the body. The term "vaginal cavity" as used herein is intended to refer to the space located between the introitus of the vagina (sometimes referred to as the sphincter of the vagina or hymeneal ring,) and the cervix. The terms "vaginal cavity," "within the vagina" and "vaginal interior," do not include the interlabial space, the floor of the vestibule or the externally visible genitalia.

The process of the present invention may be used for compressing tampons from a generally flattened pledget, and can be used for tampon shapes known in the art including but not limited the tampon disclosed in U.S. Pat. No. 6,258,075 issued to Taylor, et al on Jul. 10, 2001 and the shaped tampons disclosed in U.S. patent application Ser. No. 10/150,050 entitled "Substantially Serpentine Shaped Tampon," and U.S. patent application Ser. No. 10/150,055, entitled "Shaped Tampon," both currently pending, commonly assigned, and filed on Mar. 18, 2002. Further, the process of the present invention may be used for the tampons having secondary absorbent members, disclosed in U.S. patent application Ser. No. 10/656,489, entitled "Absorbent Tampon Comprising A Secondary Absorbent Member Attached To The Outer Surface, filed on Sep. 5, 2003. U.S. Pat. No. 6,258,075 and U.S. patent application Ser. Nos. 10/150,050, 10/150,055, and 10/656,489 are hereby incorporated by reference herein.

In another embodiment of the process, the stabilization process may be combined with a compression process. In these embodiments, the process for producing stabilized compressed tampons comprises the steps of providing a tampon pledget, providing a mold, folding and compressing the tampon pledget into the mold, forming a compressed, folded tampon pledget, and forcing a gas into the mold to stabilize the compressed, folded tampon pledget. In some embodiments, the mold provided is permeable.

The mold for compressing the tampon according to the present invention can be constructed from permeable materials or can be fabricated from impermeable or permeable materials then modified either mechanically, chemically, or electrically to become permeable. Materials for the mold may include metals, polymers and/or composites. Embodiments of the mold that are comprised of metals may include steel, stainless steel, copper, brass, titanium, alloys, aluminum, anodized aluminum, titanium and combinations thereof. Embodiments of the mold that are comprised of polymers may include TEFLON® (E.I du Pont de Nemours and Company), polyethylene, polypropylene, polyester, polyolefins, polycarbonates, nylons, polyvinyl chloride, and mixtures thereof. One embodiment of a mold may be made of DEL-RIN® made by DuPont Plastics (Wilmington, Del. USA). Embodiments of the mold that are comprised of composites may include carbon fibers and blends of metal, epoxy, ceramic and polymer blends. Other examples of suitable materials for the mold are foamed metals or plastics. The mold may be made of aluminium and epoxy porous aggregate, such as METAPOR BF100Al, available from Portec Ltd, Switzerland. Pores (if included, such as pores 22 or 220 as detailed below), interstices, or pathways can be mechanically produced in the above materials by any mechanical operation known in the art including, but not limited to, operations such as drilling, milling, punching, casting, injection molding, and the like. Chemical modification techniques may include acid etching. Electrical modification techniques may include electrical discharge machining.

The absorbent material that comprises the compressed tampon pledgets may be constructed from a wide variety of liquid-absorbing materials commonly used in absorbent articles. Such materials include but are not limited to rayon (such as GALAXY Rayon SARILLE L rayon both available from Kelheim Fibres, GmbH of Kelkeim, Germany), cotton, folded tissues, woven materials, nonwoven webs, synthetic and/or natural fibers or sheeting, comminuted wood pulp which is generally referred to as airfelt, or combinations of these materials. Other materials that may be incorporated into the tampon pledget including peat moss, absorbent foams (such as those disclosed in U.S. Pat. No. 3,994,298 issued to DesMarais on Nov. 30, 1976 and U.S. Pat. No. 5,795,921 issued to Dyer, et. al,) capillary channel fibers (such as those disclosed in U.S. Pat. No. 5,356,405 issued to Thompson, et. al on Oct. 18, 1994), high capacity fibers (such as those disclosed in U.S. Pat. No. 4,044,766 issued Kaczmarzk et al. on Aug. 30, 1977), superabsorbent polymers or absorbent gelling materials (such as those disclosed in 5,830,543 issued to Miyake, et al on Nov. 3, 1998). A more detailed description of liquid-absorbing materials shapes and dimensions can be found in U.S. patent application Ser. No. 10/039,979, filed Oct. 24, 2001, entitled "Improved Protection and Comfort Tampon," currently pending, and commonly assigned.

The compressed tampon pledget stabilized by the process of the present invention may optionally include an overwrap comprising material such as, rayon, cotton, bicomponent fibers, polyethylene, polypropylene, other suitable natural or synthetic fibers known in the art, and mixtures thereof. In some embodiments, the tampon has a nonwoven overwrap comprised of bicomponent fibers that have a polypropylene core surrounded by polyethylene manufactured by Vliesstoff-werke Christian Heinrich Sandler GmbH & Co.KG (Schwarzenbach/Saale, Germany) under the tradename SAS B31812000. In other embodiments, the tampon may comprise a nonwoven overwrap of a hydroentangled blend of 50% rayon, 50% polyester available as BBA 140027 produced by BBA Corporation of South Carolina, U.S. The overwraps may be treated to be hydrophilic, hydrophobic, wicking or non-wicking.

Tampons may optionally include a withdrawal cord, a secondary absorbent member, an additional overwrap, a skirt portion and/or an applicator. Withdrawal cords useful in the present invention may be made of any suitable material known in the prior art and include cotton and rayon. U.S. Pat. No. 6,258,075 to Taylor et al. entitled "Tampon with Enhanced Leakage Protection" describes a variety of secondary absorbent members for use in tampon pledgets. An example of a skirt portion is disclosed in U.S. patent application Ser. No. 09/993,988 entitled, "Tampon with Fluid Wicking Overwrap with Skirt Portion" currently pending, commonly assigned, and filed on Nov. 16, 2001.

The compressed tampon can be stabilized by known processes. Pressures and temperatures suitable for compression of tampons are well known in the art. Typically, the absorbent material and the overwrap (if used) are compressed in a radial or lateral direction and optionally axially by any means well known in the art. While a variety of techniques are known and acceptable for these purposes, a modified tampon compressor machine available from Hauni Machines, Richmond, Va., is suitable.

The gases forced into the tampon pledget for stabilization may be air, oxygen, nitrogen, argon, carbon dioxide, steam, ether, Freon, inert gases and mixtures thereof. Typically, steam is used. The supply of the gas may be varied by a flow control means. During the process of the present invention the gas may be propelled through the mold at a rate from about 0.2 to about 5.0 L/s. In some embodiments, the gas is propelled for time period ranging from about 1 s to about 20 s. In other embodiments, the gas is propelled for a time period ranging from about 1 s to about 10 s. In other embodiments, the gas is propelled from about 2 s to 8 s. In some embodiments a stabilization cycle of steam, heat, and cooling includes steam entry for a period of 1-2 seconds followed by a 6-15 second hold for conductive heating, and a 1-2 second cooling period before the compressed, stabilized tampon is removed from the stabilization mold.

The compressed tampon may be inserted digitally or insertion may be aided through the use of any known applicators. When the tampons are intended to be digitally inserted, it may be desirable to provide a finger indent made using a compression rod at the withdrawal end of the tampon to aid in insertion. An example of a finger indent is found in U.S. Pat. No. 6,283,952, entitled "Shaped Tampon" issued to Child, et al. on Sep. 4, 2000. Applicators that may be used are "tube and plunger" or "compact" type arrangements and may be plastic, paper, or other suitable material.

Figures 1, 2, 3, 4, 5:
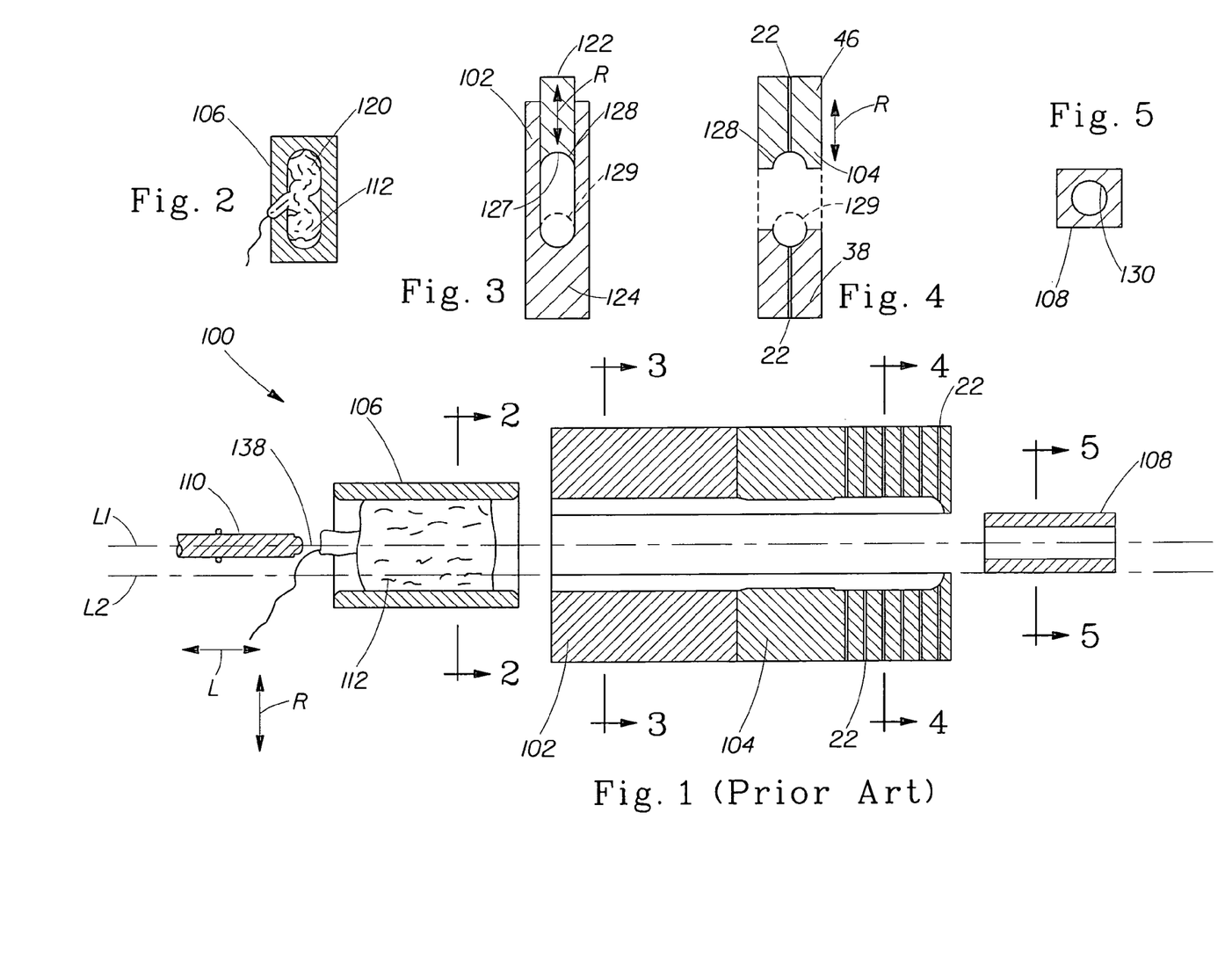
FIG. 1 is a cross-sectional view of an embodiment of a prior art apparatus for making compressed tampons.
FIG. 2 is a cross-sectional view of an infeed carrier of the apparatus of FIG. 1 taken along line 2-2.
FIG. 3 is a cross-sectional view of a compression mold of the apparatus of FIG. 1 taken along line 3-3.
FIG. 4 is a cross-sectional view of a stabilization mold of the apparatus of FIG. 1 taken along line 4-4.
FIG. 5 is a cross-sectional view of a discharge carrier of the apparatus of FIG. 1 taken along line 5-5.

FIG. 1 is a simplified longitudinal cross-sectional view a prior art embodiment 100 of a process for making a compressed tampon, including a pair of split molds: a compression mold 102 and a stabilization mold 104, as disclosed in commonly owned, co-pending U.S. patent application Ser. No. 10/717,269, filed on May 12, 2004. The embodiment 100 is particularly suitable for mass-production of stabilized tampons, wherein the steps of compressing and stabilizing of tampons are preferably separated in order to reduce the complexity of the apparatus producing stabilized tampons, especially, the tampons having a substantially serpentine shape and/or stabilized by the use of a gas.

The process shown in FIG. 1 includes both a compression mold 102 and a stabilization mold 104. Both the compression mold 102 and the stabilization mold 104 are shown in their open positions 128 and aligned with a pledget infeed carrier 106 and a tampon discharge carrier 108. In operation, compression of the tampon pledget occurs in the compression mold and then the compressed tampon is inserted by transfer member 110 into the stabilization mold for heat stabilization via pores 22.

In the apparatus 100 of FIG. 1 is shown a transfer member 110 engaging a pledget 112 disposed in the pledget infeed carrier 106. The transfer member 110 can serve several functions: (a) transferring the pledget 112 through the sequence of process steps taking place during traveling of the pledget 112 from the pledget infeed carrier 106 to the compression mold 102, to the stabilization mold 104, and to the tampon discharge carrier 108; (b) compressing the pledget 112 longitudinally (in addition to the compression in the radial or lateral direction provided by the compression die 102, as described below); (c) forming a desired shape cavity at the distal end of the tampon, suitable for the user's finger to facilitate digital insertion of the tampon into the vaginal cavity; and (d) providing a suitable seal for containing the gas inside the stabilizing die 104 during the stabilization treatment of the tampon, as described below. The transfer member 110 preferably includes at least one needle 138 extending from the transfer member 110 longitudinally for discharging a stabilized tampon from the split stabilization mold 104, as will be described in more detail below.

As shown in FIG. 1, the transfer member 110 is aligned with the pledget infeed carrier 106, the compression mold 102, the stabilization mold 104, and the tampon discharge carrier 108 along a first longitudinal centerline L1.

As shown in the cross section of FIG. 2, the tampon pledget can have a generally pre-folded "M-shape" when inserted into infeed carrier 106. However, in practice, it is difficult to ensure a consistent configuration of tampon pledget 112 in infeed carrier 106, particularly a pre-fan-folded configuration, hence the improvement of the present invention as discussed more fully below.

As shown in the cross section of FIG. 3 taken along line 3-3, tampon pledget 112 is compressed by the action of split compression mold 102 that includes a first member 122 and a second member 124. At least one of the members 122 and 124 is capable of moving in a radial direction R (radial, or lateral, with respect to the widthwise dimension of the uncompressed tampon pledget, for example) to effect an open position 128 or a closed position 129 (shown as an interrupted line) of the split compression mold 102. In the closed position 129, the inner surface 127 of the compression mold 102 forms preferably a circular cross-section of a desired diameter, for example, a diameter of 12.5 mm. However, the inner surface 127 can be of any suitable shape and of any desired dimension. The split compression mold 102 can be made from any materials capable of providing desired compression forces and suitable for producing sanitary tampons.

FIG. 4 is a simplified radial cross-sectional view of the split stabilization mold 104 of FIG. 1, taken along line 4-4. The split stabilization mold 104 can include first member 38, second member 46, and at least one pore 22 suitable for providing a gas flow inside the inner surface of the stabilization mold 104. The split stabilization mold 104 is shown in the open position 128 when the first member 38 and the second member 46 are separated from each other. At least one of the mold members 38 and 46 can move in the radial direction R to effect the open position 128 or the closed position 129 (shown as an interrupted line) when the first member 38 and the second member 46 are in contact with each other.

FIG. 5 is a simplified radial cross-sectional view of a tampon discharge carrier 108 of FIG. 1, taken along line 5-5. The tampon discharge carrier 108 includes a cavity 130 that can be suitably dimensioned and shaped to accept the compressed and stabilized tampon. The tampon discharge carrier 108 can be a part of, or feed into, further processing equipment for wrapping, packaging, or otherwise preparing the tampon for sale to a consumer.

It should be noted that a pledget having a secondary absorbent member extending from the distal end of the pledget (as noted above), should be loaded into the pledget infeed carrier with the secondary absorbent member being diverted radially in relation to the pledget to ensure that the secondary absorbent member does not interfere with the movement of the transfer member 110 in order to prevent pushing the secondary absorbent member into the distal end of the pledget. The radial diversion of the secondary absorbent member (preferably, together with at least one cord extending also from the distal end of the tampon) can be provided during loading of the pledget 112 by any suitable means, for example, a plate disposed in the direction of loading of the pledget into the cavity of the infeed carrier.

Figures 6, 7, 8, 9, 10:
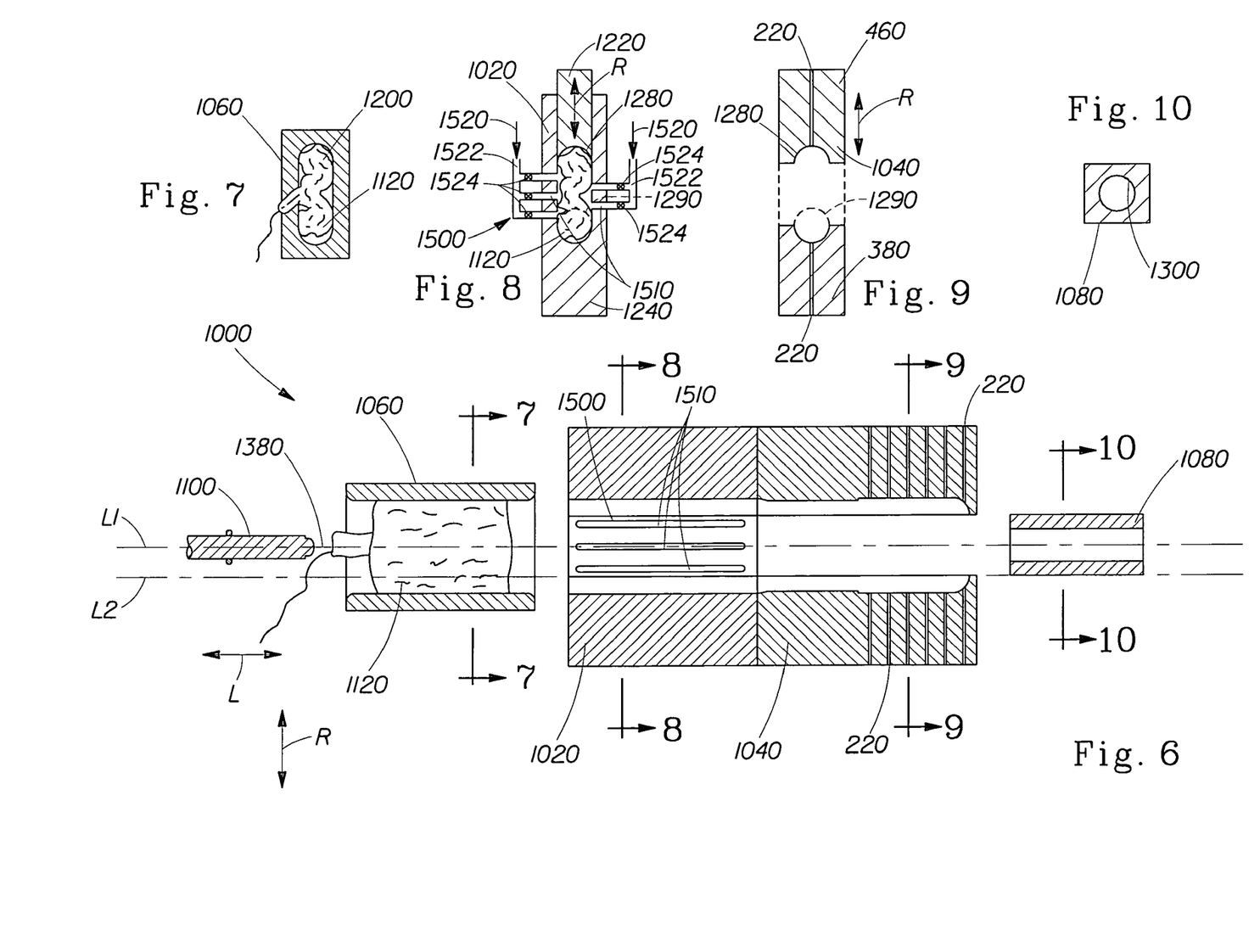
FIG. 6 is a cross sectional view of an embodiment of an apparatus of the present invention for making compressed tampons from a pledget folded into a generally zigzag profile.
FIG. 7 is a cross-sectional view of an infeed carrier of the apparatus of FIG. 6 taken along line 7-7.
FIG. 8 is a cross-sectional view of a compression mold of the apparatus of FIG. 6 taken along line 8-8.
FIG. 9 is a cross-sectional view of a stabilization mold of the apparatus of FIG. 6 taken along line 9-9.
FIG. 10 is a cross-sectional view of a discharge carrier of the apparatus of FIG. 6 taken along line 10-10

FIG. 6 is a simplified longitudinal cross-sectional view an apparatus 1000 of the present invention showing the improvement of the present invention over the prior art apparatus shown in FIG. 1. In FIG. 6 is shown an apparatus and method for making a compressed tampon from a generally flat tampon pledget 1120. The apparatus 1000 includes a pair of split molds: a compression mold 1020 and a stabilization mold 1040 as well as other features common to the apparatus shown and described in FIG. 1 above, and denoted in FIG. 6 with the addition of a "0" on the identifying number.

In the prior art apparatus and method described with respect to FIG. 1 above, it has been found that even if pre-folded in the infeed carrier 106, pledget 112 tends to not fold consistently during compression. In particular, during transfer of the pledget from infeed carrier 106 to compression mold 102, pledgets tended to flatten back out to an unfolded condition, which results in unwanted folding at pledget edges, unwanted material interference (i.e., jams) during compression, as well as inconsistent fold configurations during compression. For example, when pre-folded in the infeed carrier, pledgets have stored energy that tends to make the pledget expand and interfere with parts and equipment during transfer into and out of the infeed carrier.

As shown in FIG. 6, the apparatus of the present invention is designed to overcome the problems of the prior art apparatus and method by providing for a more uniformly fan-folded tampon pledget by the addition of folding means 1500 to compression mold 1020. By placing the pledget in the infeed carrier 1060 in an unfolded state, the pledget can be transferred without the expansion forces associated with a pre-folded pledget, enabling smoother transfer in and out of infeed carrier 1060. Once inside compression mold 1020, pre-folding occurs at the point of compression, thereby facilitating greater control of folding for better uniformity of fold configuration upon compression.

Folding means 1500 can comprise fluid communication passages and force delivery means for delivering pressure to predetermined portions of the tampon pledget. Fluid communication passages can comprise holes or slots 1510 and force delivery means can comprise mechanical folding pins, fins, or, as illustrated, pneumatic or other fluid impingement folding means, and in either embodiment the force delivery means serves the function of accurately, consistently, and predictably pre-folding the tampon pledget into a generally zigzag or fan-folded shape such that upon compression the folds are of uniform and repeatable dimensions and the pledget compresses uniformly. This is because folding is accomplished at the same place as compression.

As shown in more detail in FIG. 8, compression mold 1020 (shown in cross section, corresponding to and showing the novel features added to the compression mold 102 shown in the cross section of FIG. 3) can be configured to have a force delivery means such that a force can be applied at predetermined portions of the tampon pledget so as to urge the pledget into at least one linear fold at a desired position prior to compression. The force delivered via the force delivery means can be due to solid on solid interaction or fluid (e.g., gas) on solid interactions. For either force delivery means, compression mold 1020 can have fluid communication means, i.e., access through the mold wall in the form of holes or slots 1510, such the interior cavity and the outside of the mold can be in fluid communication. Fluid communication means can be aligned generally parallel to longitudinal axis L1 and at least partially along, and in one embodiment extending along substantially all of, the length of compression mold 1020, as shown in FIG. 6. Holes can be used for fluid communication means, including a plurality of spaced apart holes, in addition to or instead of slots. In one embodiment referred to as "solid on solid" force delivery, some or all of the holes or slots can have pins or flattened fins operatively positioned so as to be moveable or extendable from outside the interior cavity of the compression mold 1020, to physically urge the tampon pledget into a partially folded configuration, so as to urge the pre-compressed pledget into a pre-folded configuration, and then be retracted prior to the first member 1220 of the mold closing.

In another embodiment fluid communication means can comprise slots. Slots 1510 permit folding by facilitating generally linear fluid communication access to the interior of compression mold 1020 such that a tampon pledget therein can be contacted by a force delivery means along a line of pressure and thereby urged into a linear fold at a desired position prior to compression. This is referred to as "fluid on solid" force delivery, and has the advantage of avoiding any chance of unwanted physical solid interference between first member 1220 and the force delivery means upon lateral movement of the first member 1220 cross die.

As can be seen in the cross-section of FIG. 8, slots 1510 can be placed in mold 1020 such that the slots on opposing sides of the mold 1020 (the right and left sides as viewed in FIG. 8) are vertically offset. By vertically offsetting opposing slots 1510, folding means 1500 facilitates zigzag folding of tampon pledget 1120. In general, the number of slots can equal the number of fold segments. Depending on the size and other geometrical characteristics of tampon pledget 1120, more or less slots can be used for a given number of desired fold panels. In general the number of slots or rows of holes can equal the number of panels in a fan-folded structure plus or minus 1. Therefore, for an "M" shaped folding pattern with four fold panels, five slots can be utilized, two to tuck the points of the "M" and three to push in the middle and the "legs" of the "M". In some cases the number of slots necessary can be equal to the number of desired fold panels minus one, as shown in FIG. 8. In FIG. 8, tampon pledget 1120 is folded into six fold panels by the use of five slots. Other fold configurations can be achieved simply by varying the length, width, and position of slots 1510, as well as the volume, pressure, type, and timing of fluid pressure impingement, as described more fully below.

The number and placement of slots or rows of holes 1510 can also be limited in placement and length so as to provide different folding configurations along the length of the tampon. For example, in one embodiment, slots 1510 can be disposed on only one side of mold 1020, such as the left or right side as depicted in FIG. 8. In such an embodiment one or more folds can be effected on one side of tampon pledget prior to tampon compression. In another embodiment, slots 1510 can be positioned so as to be adjacent only the end of the tampon pledget from which the withdrawal cord extends. In this manner, the lower portion of a compressed tampon would have more pronounced fan-folding than the top portion which might have none. Likewise, slots 1510 can be disposed to effect folding on only the upper portion of a tampon or only in the center of the tampon. In this manner, the expansion characteristics of a folded, compressed tampon can be adjusted and predetermined to provide for the best expansion and fluid handling properties in use. In another embodiment, the mold cavity can be defined as having a first end and a second end, the first and second ends corresponding to the two ends of a generally cylindrical tampon, such as the insertion end and the withdrawal end. In this embodiment, the fluid communication passages can be disposed on the compression mold such that the passages are disposed nearer one or the other of the first or second ends, such that the compressed tampon has more pronounced fan-folding on only one end thereof. For example, in one embodiment, a compressed tampon having a fan-folded withdrawal end and a non-folded insertion end (the end that enters the body first upon proper insertion).

Further, in one embodiment, the time of delivery or actuation of the force delivery means can be varied in a predetermined manner such that a first force delivery means is activated in a first set of fluid communication passages, and thereafter a second force delivery means is activated in a second set of fluid communication passages. In this manner, for example, valves for air pressure can be actuated in a timing sequence such that a central fold near the longitudinal center of the tampon pledget can be effected prior to additional folds, which can be successively effected by varying the timing of successive actuations of force delivery means.

In one embodiment, folding means 1500 can comprise a plurality of mechanical pins (not shown), each pin being either round or flattened and elongated to fit into fluid communication passages, i.e., slots 1510. Pins can extend into mold 1020 to physically force the tampon pledget into a generally fan-folded shape, and then retract prior to compression by the movement of split mold part 1220. However, in one embodiment believed to be more reliable, folding means can be provided by fluid pressure, such as air pressure supplied in a controlled manner through slots 1510. In addition to air, the fluid can be a gas is selected from the group consisting of air, oxygen, nitrogen, argon, carbon dioxide, steam, ether, Freon, inert gases and mixtures thereof.

In one embodiment, each slot 1510 can be pneumatically operatively connected to fluid supply, such as an air supply 1520 that can be actuated so that the force delivery means is air pressure impinging upon tampon pledget 1120 inside mold 1020. By "pneumatically operatively connected" is meant that a slot is connected to a fluid supply, such as an air or other gas supply, by pipes, tubes, connectors, and controlled by known means to deliver air or other gas through slots upon demand. While in theory any fluid could be used, the description herein shall be with respect to air as the fluid medium. In general, clean, dry (i.e., <about 50% relative humidity at room temperature) air can be used to effect the fan-folded configuration of tampon pledget inside mold 1020. Volume, pressure, and time of actuation can each be varied as required for folding as desired.

Air can be delivered as compressed air via manifolds 1522 and regulated by valves 1524. Valves 1524 can be controlled by known means to permit air to enter the compression chamber in any controlled manner. In one embodiment all valves 1524 open and close simultaneously. In another embodiment, all valves 1524 open to permit the same volume and pressure of air into the compression chamber. In another embodiment, the timing of each valve 1024 opening can be predetermined such that certain valves 1524 open and/or close independently of other valves 1524 opening or closing. In another embodiment, the air volume and/or pressure of each valve can be predetermined such that certain valves 1524 have air volume and/or pressure independently of other valves 1524 opening or closing.

As shown in the comparison of FIGS. 7 and 8, tampon pledget 112 can be delivered to infeed carrier in a generally flattened pledget as a batt of fibers. Once delivered into compression mold 1020 but before application of air pressure, tampon pledget 1120 keeps its generally flattened shape. After tampon pledget 1120 is in the compression mold and coincidental with or before compression by moving first member 1220, air pressure can be delivered with sufficient volume and force so as to impinge on alternate sides of tampon pledget 1120 to cause it to take a generally zigzag shape shown in FIG. 8. Air pressure can continue to impinge upon tampon pledget 1120 until tampon 1102 is compressed.

In one embodiment, air pressure is delivered uniformly and simultaneously to slots 1510. In another embodiment, air pressure is delivered with greater volume and pressure in one or more slots relative to one or more other slots. It is believed that by varying the air flow volume and pressure in this manner, the final compressed fold configuration can be improved in its expansion properties. Likewise, the delivery of air volume and pressure to certain of slots 1510 can be varied in time, such that certain slots conduct air pressure to tampon pledget before other slots. In this manner, it is believed that the final compressed fold configuration can be improved in its expansion properties. In another embodiment, air pressure can be delivered to only one side of mold 1020, so that force delivery is provide on one side of tampon pledget 1200.

FIG. 9 is a simplified radial cross-sectional view of the split stabilization mold 1040 taken along line 9-9. The split stabilization mold 1040 can be similar in the dimensions and makeup, in all or any aspects, to the split mold shown in FIG. 4. For example, the split stabilization mold 1040 includes a first member 380, a second member, e.g., a closing die 460, and at least one pore 220 suitable for providing a gas flow inside the inner surface of the stabilization mold 1040. The split stabilization mold 1040 is shown in the open position 1280 when the first member 380 and the second member 460 are separated from each other. At least one of the mold members 380 and 460 can move in the radial direction R to effect the open position 1280 or the closed position 1290 (shown as an interrupted line) when the first member 380 and the second member 460 are in contact with each other.

FIG. 10 is a simplified radial cross-sectional view of a tampon discharge carrier 1080 taken along line 10-10. The tampon discharge carrier 1080 includes a cavity 1300 that can be suitably dimensioned and shaped to accept the compressed and stabilized tampon.

Figure 11:
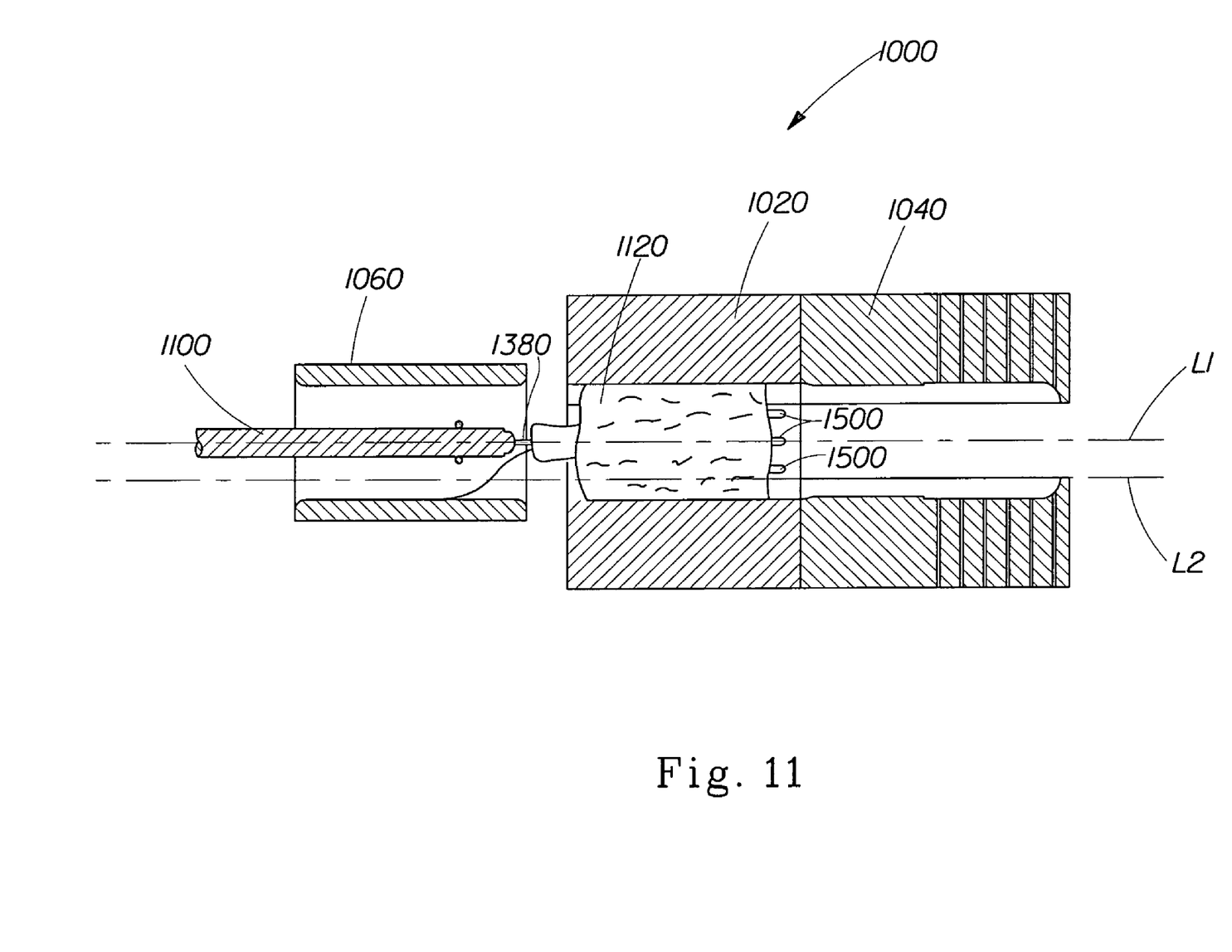
FIG. 11 is a simplified longitudinal cross-sectional view of an apparatus of the present invention showing a tampon pledget being loaded into a split compression mold by a transfer member, the split compression mold being in an open position.

FIG. 11 is a simplified longitudinal cross-sectional view of the embodiment 1000 of FIG. 6, showing the pledget 1120 being loaded into the split compression mold 1020 by the transfer member 1100 when the split compression mold 1020 is in the open position 1280 and the transfer member 1100 is aligned with the first longitudinal centerline L1. In the open position the compression mold 1020 has an inside dimension that can be any dimension suitable for accepting the pledget 1120.

Figure 12:
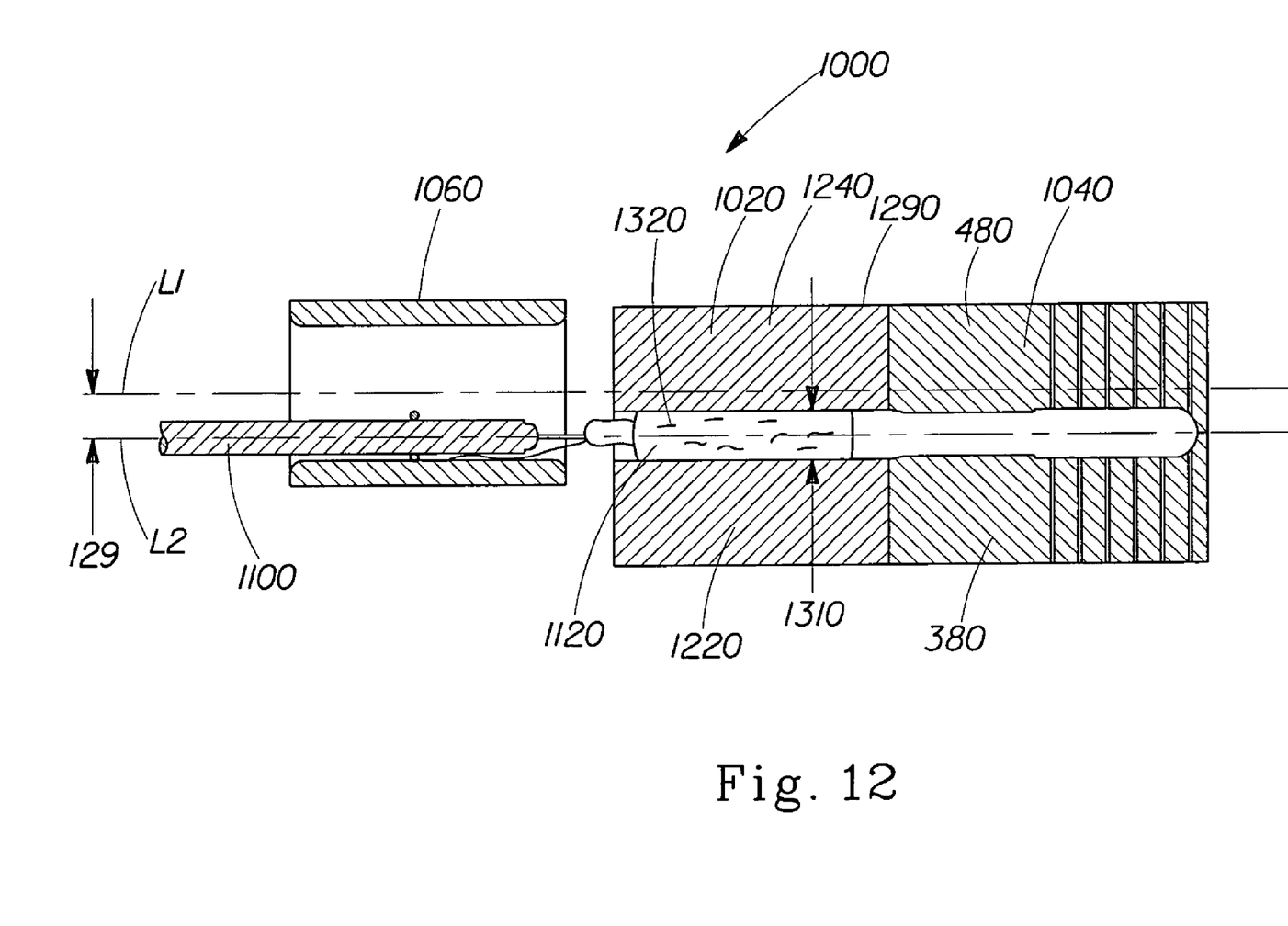
FIG. 12 is a simplified longitudinal cross-sectional view of an apparatus of the present invention showing a tampon pledget being compressed into a compressed tampon.

FIG. 12 is a simplified longitudinal cross-sectional view of the embodiment 100 of FIG. 6, showing the pledget 1120 being compressed into a compressed tampon 1320 in the compression mold 1020 when the compression mold 1020 is in the closed position. In the closed position the compression mold 1020 has an inside dimension 1310 that can be any dimension suitable for compressing the pledget 1120 into a desired compressed dimension. For example, in one embodiment of the invention, the inside dimension 1310 can be a diameter of a circular cross section and can be about 12.5 mm.

As shown in FIG. 12, the transfer member 1100 can also move in the radial direction R to become aligned along a second longitudinal centerline L2 aligned with the closed position 129 of the compression mold 1002. The distance between the first longitudinal centerline L1 and the second longitudinal centerline L2 is a dimension 129, which is preferably about half of the radial movement of the first compression mold member 1220. For example, in one embodiment, the first compression mold member 1220 can move about 28 mm, and the transfer member 1100 can move a distance 129 of about 14 mm.

Figure 13:
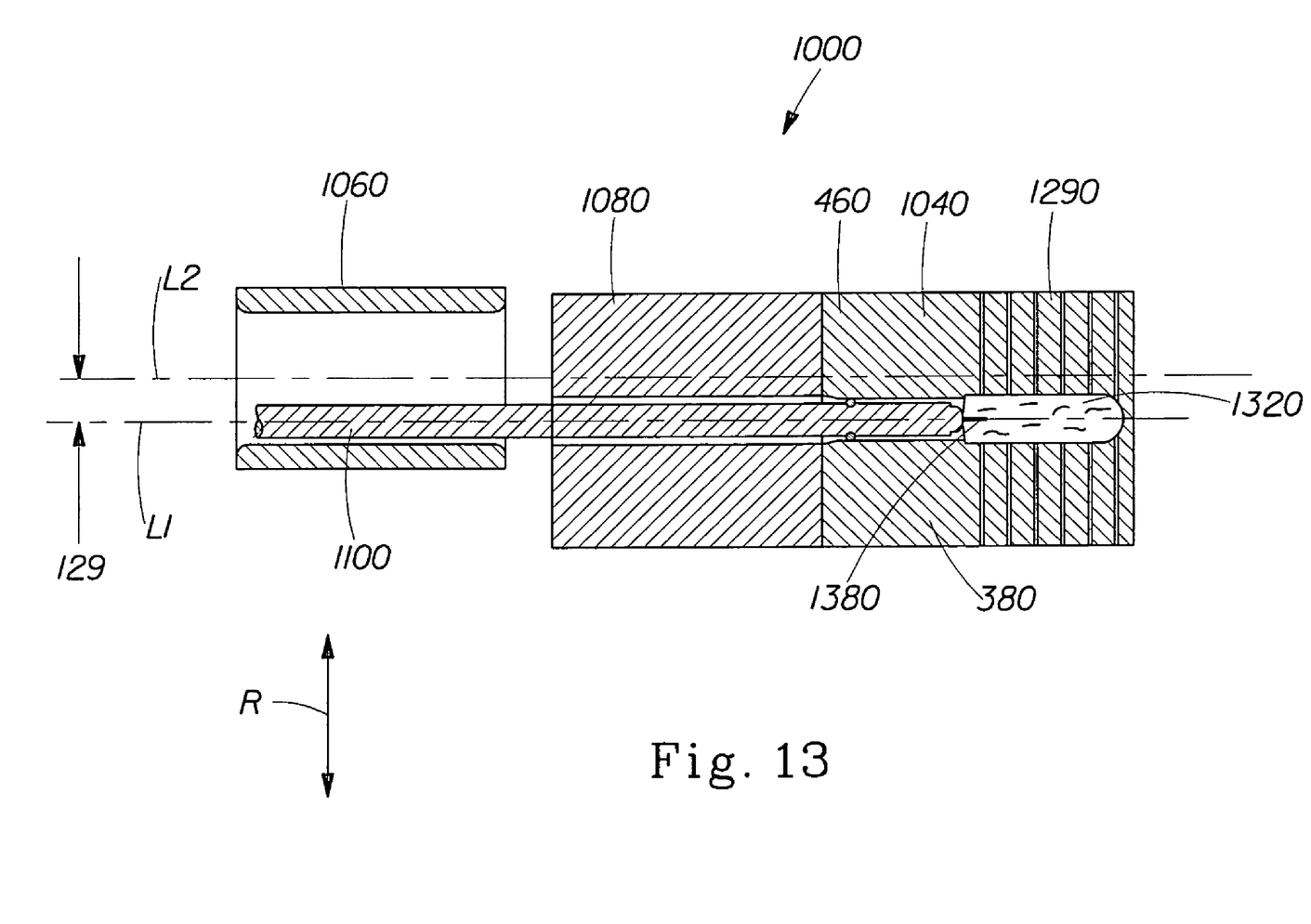
FIG. 13 is a simplified longitudinal cross-sectional view of an apparatus of the present invention showing a compressed tampon being loaded into a stabilization mold.

FIG. 13 is a simplified longitudinal cross-sectional view of the embodiment 1000 of FIG. 6, showing the compressed tampon 1320 being loaded into the split stabilization mold 1040 by the transfer member 1100, when the split stabilization mold 1040 is preferably in the closed position and axially aligned with the second longitudinal centerline L2. In a preferred embodiment, the closed position of the stabilization mold 1040 is accomplished by moving the first member 460 of the stabilization mold 1040 in the radial direction R simultaneously with the first compression mold member 1220. However, as was noted above with respect to the compression mold 1020, the stabilization mold 1040 can also include two moving mold members. Furthermore, in other contemplated embodiments of the present invention, the compression mold 1020 and the stabilization mold 1040 do not need to close and open simultaneously.

As noted above, the transfer member 1100 preferably includes at least one needle 1380 extending from the transfer member 1100 longitudinally. The needle(s) 1380 are capable of penetrating into the compressed tampon to enable a subsequent discharge of the stabilized tampon from the stabilization mold 1040. The number of needles 1380 can include any suitable number, preferably two needles to prevent turning of the tampon around a single needle around a longitudinal direction of the tampon.

After stabilization, the compressed, stabilized tampon can be unloaded by the use of a transfer member 1100 into the tampon discharge carrier 1080 and further processed by means known in the art for tampon production, such as to a rotary apparatus described in the above mentioned co-pending U.S. patent application Ser. No. 10/717,269, filed on May 12, 2004.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for producing a stabilized tampon from a tampon pledget, the method comprising the steps of:
   a. providing a tampon pledget;
   b. providing a compression mold having disposed therein a plurality of fluid communication passages;
   c. moving said tampon pledget into said compression mold by a transfer member, said compression mold being in an open position;
   d. applying fluid pressure through said fluid communication passages to deform said tampon pledget into a pre-folded shape; and
   e. compressing said pledget in said compression mold by closing said compression mold into a closed position to form a folded, compressed tampon.

2. The method of claim 1, further comprising the steps of:
   a. unloading said compressed tampon from said compression mold and loading said compressed tampon into a stabilization mold, said stabilization mold being in a closed position;
   b. applying a gas to said compressed tampon in said stabilization mold to form a stabilized tampon;
   c. opening said stabilization mold into an open position; and
   d. loading said stabilized tampon into a tampon discharge carrier.

3. The method of claim 1, wherein said fluid is selected from the group consisting of air, oxygen, nitrogen, argon, carbon dioxide, steam, ether, Freon, inert gases and mixtures thereof.

4. The method of claim 2, wherein said gas is selected from the group consisting of air, oxygen, nitrogen, argon, carbon dioxide, steam, ether, Freon, inert gases and mixtures thereof.

5. The method of claim 1, wherein said fluid communication passages comprise slots.

6. The method of claim 1, wherein said compression mold comprises first and second opposing sides and in which said fluid communication passages are disposed on said opposing sides of said mold, and wherein said fluid communication passages on said first opposing side of said mold are offset relative to fluid communication passages on said second opposing side of said mold.

7. A method for producing a stabilized tampon from a tampon pledget, the method comprising the steps of:
   a. providing a tampon pledget;
   b. providing a compression mold having disposed therein on at least two sides thereof a plurality of fluid communication passages;
   c. providing a force delivery means;
   d. moving said tampon pledget into said compression mold by a transfer member, said compression mold being in an open position;
   e. applying force to said tampon pledget by said force delivery means through said fluid communication passages to deform said tampon pledget into a pre-folded shape;
   f. compressing said pledget in said compression mold by closing said compression mold into a closed position to form a folded, compressed tampon.

8. The method of claim 7, further wherein:
   g. said plurality of fluid communication passages comprises at least a first set of fluid communication passages and a second set of fluid communication passages; and prior to said compressing step:
   h. applying a first force delivery means through said first set of fluid communication passages; and, after a predetermined amount of time,
   i. applying a second force delivery means through said second set of fluid communication passages.

9. The method of claim 7, wherein said force delivery means is a pressurized fluid selected from the group consisting of air, oxygen, nitrogen, argon, carbon dioxide, steam, ether, Freon, inert gases and mixtures thereof.

10. The method of claim 7, wherein said fluid communication passages comprise slots.

11. The method of claim 7, wherein said compression mold comprises first and second opposing sides and in which said fluid communication passages are disposed on said opposing sides of said mold.

12. The method of claim 11, wherein said fluid communication passages on said first opposing side of said mold are offset relative to fluid communication passages on said second opposing side of said mold.

13. The method of claim 11, wherein said compression mold defines an inner cavity in which said tampon pledget is compressed, said inner cavity having a first end and a second end, said first and second ends corresponding to the two ends of a compressed tampon, said plurality of fluid communication passages being disposed nearer said first end of said cavity than said second.

* * * * *